United States Patent
Hoeger et al.

(12)

(10) Patent No.: US 12,290,427 B2
(45) Date of Patent: May 6, 2025

(54) MULTILAYERED TEXTILE MATERIAL FOR CONTAINING LIQUIDS AND ASSOCIATED SYSTEMS AND METHODS

(71) Applicants: Cherie Hoeger, Meridian, ID (US); Jonathan Hoeger, Meridian, ID (US)

(72) Inventors: Cherie Hoeger, Meridian, ID (US); Jonathan Hoeger, Meridian, ID (US)

( * ) Notice: Subject to any disclaimer, the term of this patent is extended or adjusted under 35 U.S.C. 154(b) by 1174 days.

(21) Appl. No.: 17/065,458

(22) Filed: Oct. 7, 2020

(65) Prior Publication Data

US 2022/0104976 A1    Apr. 7, 2022

(51) Int. Cl.
| | |
|---|---|
| A61F 13/537 | (2006.01) |
| A61F 13/14 | (2006.01) |
| A61F 13/15 | (2006.01) |
| A61F 13/496 | (2006.01) |
| A61F 13/53 | (2006.01) |
| A61F 13/534 | (2006.01) |

(52) U.S. Cl.
CPC ...... *A61F 13/53704* (2013.01); *A61F 13/141* (2013.01); *A61F 13/15203* (2013.01); *A61F 13/496* (2013.01); *A61F 13/53708* (2013.01); *A61F 2013/15016* (2013.01); *A61F 2013/15422* (2013.01); *A61F 2013/530445* (2013.01); *A61F 2013/53445* (2013.01)

(58) Field of Classification Search
CPC ........ A61F 13/14; A61F 13/15; A61F 13/496; A61F 13/53; A61F 13/534; A61F 13/537
See application file for complete search history.

(56) References Cited

U.S. PATENT DOCUMENTS

| | | | |
|---|---|---|---|
| 3,717,150 A * | 2/1973 | Schwartz | ............. A61F 13/515 604/383 |
| 5,306,536 A | 4/1994 | Moretz et al. | |
| 5,315,717 A | 5/1994 | Moretz et al. | |
| 5,414,870 A | 5/1995 | Moretz et al. | |
| 5,522,811 A * | 6/1996 | Igaue | ..................... A61L 15/24 604/383 |

(Continued)

FOREIGN PATENT DOCUMENTS

WO    2014022832 A1    2/2014

OTHER PUBLICATIONS

Examination Report mailed Jul. 19, 2024 in United Kingdom Patent Application No. GB2305584.1, 2 pages.

(Continued)

*Primary Examiner* — Michele Kidwell

(57) ABSTRACT

A reusable textile material for managing a bodily fluids and associated systems and methods are disclosed herein. In some embodiments, the textile material includes a first layer having an inner surface and an outer surface, a second layer in contact with the outer surface of the first layer, and a third layer opposite the second layer from the first layer. In some embodiments, the first layer is configured to draw the bodily fluid through the first layer from the inner surface to the outer surface while dispersing the bodily fluid laterally across the first layer. In some embodiments, the second layer is configured to pull the bodily fluid away from the outer surface and hold the bodily fluid in the second layer. In some embodiments, the third layer is configured to confine the bodily fluid from in the second layer.

18 Claims, 8 Drawing Sheets

(56) References Cited

U.S. PATENT DOCUMENTS

| | | | |
|---|---|---|---|
| 5,906,876 A * | 5/1999 | Conway | A41B 17/00 428/95 |
| 5,946,726 A | 9/1999 | Green | |
| 6,274,218 B1 * | 8/2001 | Shimizu | A61F 13/512 428/137 |
| 6,432,504 B1 | 8/2002 | Yeh | |
| 6,515,195 B1 | 2/2003 | Lariviere et al. | |
| 8,127,575 B2 | 3/2012 | Burrow et al. | |
| 8,424,118 B2 | 4/2013 | Maxey et al. | |
| 8,821,467 B1 * | 9/2014 | Minella | A61F 13/49004 604/385.15 |
| D716,020 S | 10/2014 | Dunbar et al. | |
| 9,687,395 B2 | 6/2017 | Clarke | |
| 10,501,873 B2 | 12/2019 | Hurd et al. | |
| 10,640,915 B2 | 5/2020 | Xing et al. | |
| 10,750,793 B1 | 8/2020 | Theodoridis | |
| 10,786,016 B2 | 9/2020 | Caden | |
| 2004/0229008 A1 * | 11/2004 | Hoying | B32B 5/06 428/394 |
| 2005/0075027 A1 * | 4/2005 | Etchells | B32B 5/147 442/205 |
| 2006/0100597 A1 | 5/2006 | Miskie | |
| 2006/0122572 A1 * | 6/2006 | Suarez | A61F 13/53704 604/385.101 |
| 2010/0121300 A1 | 5/2010 | Hann | |
| 2016/0067118 A1 * | 3/2016 | Hammons | B32B 3/30 428/137 |
| 2016/0175171 A1 * | 6/2016 | Brumm | A61F 13/53708 604/378 |
| 2016/0242972 A1 * | 8/2016 | Clarke | A61L 15/425 |
| 2016/0296384 A1 | 10/2016 | Png et al. | |
| 2018/0279694 A1 * | 10/2018 | Theno | A41B 9/12 |
| 2020/0248400 A1 * | 8/2020 | Xing | B32B 5/024 |

OTHER PUBLICATIONS

International Preliminary Report on Patentabillity mailed Apr. 20, 2023 in International Patent Application No. PCT/US21/53404, 9 pages.

International Search Report and Written Opinion mailed Jan. 24, 2022 in International Patent Application No. PCT/US21/53404, 12 pages.

* cited by examiner

MULTILAYERED TEXTILE MATERIAL FOR CONTAINING LIQUIDS AND ASSOCIATED SYSTEMS AND METHODS

TECHNICAL FIELD

The present technology is generally directed to a textile material that absorbs fluids, and more particularly to a textile material that disperses and holds bodily fluids away from a skin-contacting surface of the textile material, and garments including the same.

BACKGROUND

While the emission of some bodily fluids can be addressed by moisture wicking fabrics that move the bodily fluids to an outer surface of the fabric to evaporate, some bodily fluids must be discretely contained and managed. For example, breast milk, menstrual fluids, and/or urine cannot be conveniently addressed by moisture wicking fabrics. Rather, these bodily fluids must be discretely contained by absorbing the bodily fluid into a fabric or other absorbent material concealed underneath or integrated into clothing. However, bodily fluids absorbed into fabric are typically held against the skin of the user, which can result in user discomfort. In some instances, moisture from the bodily fluids held against the skin can even cause rashes and infections on the skin.

Figure 1:
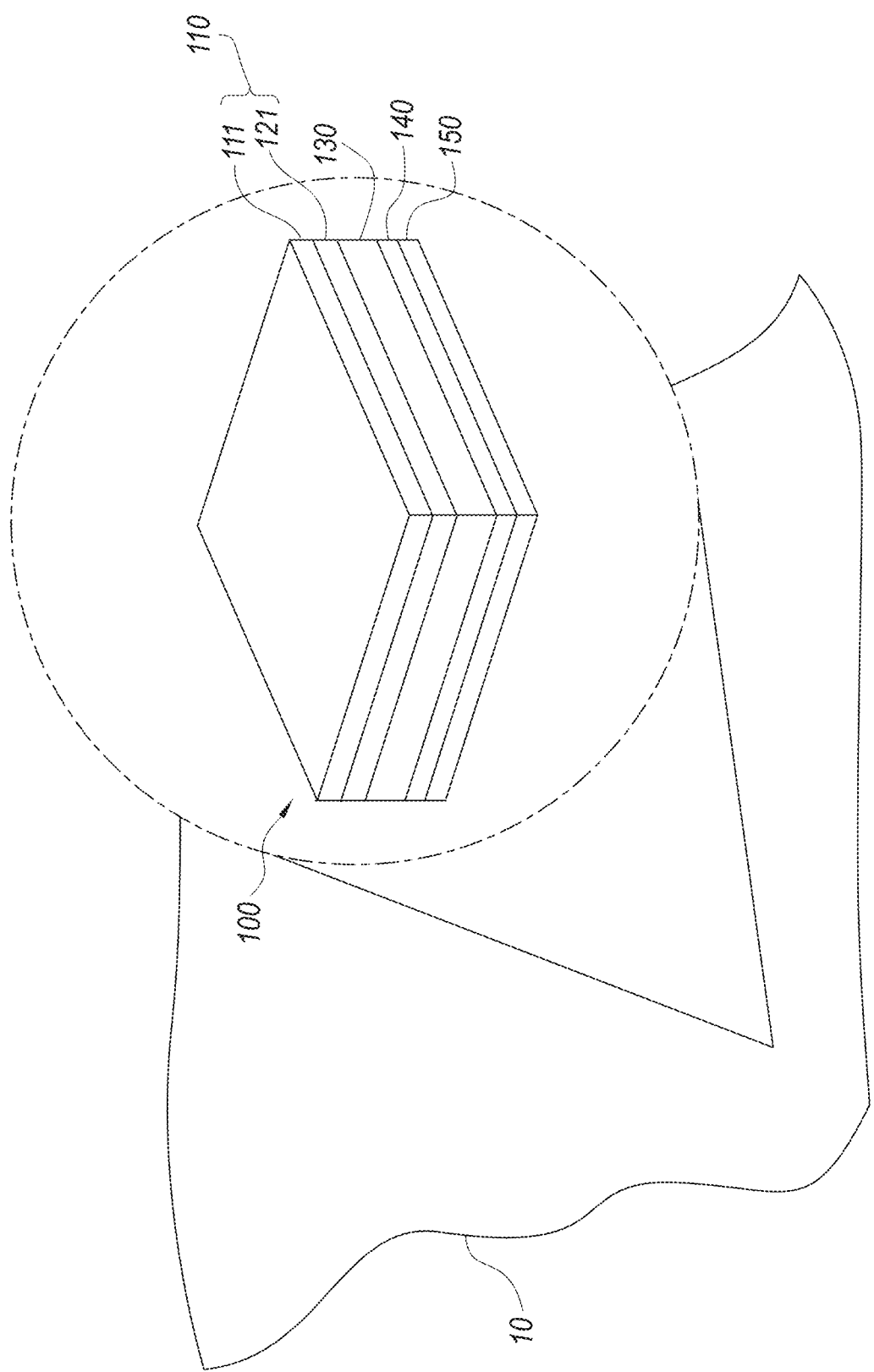
FIG. 1 is a partially sectional view of a textile material in accordance with some embodiments of the present technology.

The drawings have not necessarily been drawn to scale. Similarly, some components and/or operations can be separated into different blocks or combined into a single block for the purpose of discussion of some of the implementations of the present technology. Moreover, while the technology is amenable to various modifications and alternative forms, specific implementations have been shown by way of example in the drawings and are described in detail below. The intention, however, is not to limit the technology to the particular implementations described. On the contrary, the technology is intended to cover all modifications, equivalents, and alternatives falling within the scope of the technology as defined by the appended claims.

DETAILED DESCRIPTION

Overview

A multilayered, reusable textile material and related systems and methods for dispersing, transporting, and storing liquid, such as a bodily fluid, away from the skin are disclosed herein. The textile material can be integrated into various garments to transport the bodily fluid to a layer separated from the skin by a distance and hold the bodily fluid therein. For example, in some embodiments, the textile material can be integrated into underwear to be worn during or near menstruation. Menstrual fluids incident on a skin-facing surface can be dispersed and transported to an interior layer that absorbs and holds the fluid a distance away from the skin-facing surface, thereby allowing the skin-facing surface to remain substantially dry and thereby increasing a user's comfort. In various embodiments, the textile material can be integrated into the crotch or other regions of underwear, swimwear, shorts, compression shorts, and/or pants; the cup, nipple, armpit or other regions of bras, swimwear, shirts, and/or jackets; and/or regions of towels, blankets, cloths, etc. to collect various other fluids as well, such as sweat, urine, breast milk, blood, pus, water, spilled liquids, etc.

For ease of reference, the textile material is sometimes described herein with reference to top and bottom, upper and lower, upwards and downwards, and/or horizontal plane, x-y plane, vertical, or z-direction relative to the spatial orientation of the embodiments shown in the figures. It is to be understood, however, that the textile material can be moved to, and used in, different spatial orientations without changing the structure and/or function of the disclosed embodiments of the present technology.

Further, although primarily discussed herein as a textile material that can be integrated into various garments to absorb and manage bodily fluids, one of skill in the art will understand that the scope of the invention is not so limited. For example, the textile material can also be integrated into various other cloths, such as towels, blankets, sheets, etc., and is capable of absorbing various other liquids, such as water and/or spilled drinks. In some embodiments, the textile material may also be a separate element—for example, as an element that can be worn inside of a garment (e.g., a menstrual pad, a nipple pad, a sweat pad, etc.). Accordingly, the scope of the invention is not confined to any subset of embodiments, and is confined only by the limitations set out in the appended claims. In addition, although primarily described herein with reference to water resistance, hydrophilicity, hydrophobicity, etc., the relevant properties of the layers and/or sublayers may be configured with reference to the resistance to or promotion of movement of liquids other than water and/or contact angles formed by liquids other than water. Accordingly, terms such as water resistance, hydrophilicity, hydrophobicity, etc. should be understood to refer to the relevant properties with respect to any and/or all fluids, unless specifically indicated otherwise.

In some embodiments, the textile material includes four layers. The first layer (also described as the "skin-facing layer," the "innermost layer," and/or the "top" or "uppermost layer") can include a first and second sublayers that work in combination to disperse a bodily fluid incident on the upper surface (e.g., the inner surface) in a horizontal direction (e.g. laterally across the upper surface) while drawing the fluid downwards towards a lower surface (e.g., the outer surface). The second sublayer can further disperse the bodily fluid in the horizontal direction while also further drawing the bodily fluid in the vertical direction. The second layer is attached to the first layer and can include a liquid absorbing material (e.g., a hydrophilic material, hygroscopic material, or other suitable material). The second layer can absorb bodily fluid from the first layer and hold the bodily fluid in the second layer some distance from the innermost surface. The third layer is attached to the second layer opposite the first layer and can include a material that at least partially confines the bodily fluid to the second layer by resisting the bodily fluid from passing through it (e.g., a leak resistant material, a moisture resistant material, water resistant material, water-proof material, etc.). Accordingly, the third layer can resist the flow of bodily fluid out of the second layer. The fourth layer is attached to the third layer opposite the second layer and can include a fabric that is used in, or is matched to other fabrics used in, the construction of the rest of a garment. The fabric can be on the outermost surface of the textile material in order to visually blend the textile material into the rest of the garment.

Description of the Figures

Many of the details and features shown in the Figures are shown schematically and/or are merely illustrative of particular embodiments of the technology. Accordingly, other embodiments can have other details and features without departing from the spirit and scope of the present technology. Furthermore, various embodiments of the technology can include structures other than those illustrated in the Figures and are expressly not limited to the structures shown in the Figures. Moreover, the various elements and features illustrated in the Figures may not be drawn to scale. In the Figures, similar reference numbers identify identical or at least generally similar elements.

FIG. 1 is a partially sectional view of a textile material 100 in accordance with some embodiments of the present technology. In the illustrated embodiment, the textile material 100 includes a first layer 110 having a first sublayer 111 (e.g., a hydrophobic sublayer) and a second sublayer 121 (e.g., a hydrophilic sublayer), a second layer 130 (e.g., an absorbent layer), a third layer 140 (e.g., a leak-resistant layer), and a fourth layer 150 (e.g., a fashion-specific outer layer). In some embodiments, each layer of the textile material 100 can be manufactured in large sheets and/or rolls, which can then be used to form the textile material 100. In some embodiments, the large sheets and/or rolls are then stacked and/or sewn together at the edges and in various portions throughout, thereby allowing the textile material 100 to be easily incorporated into the production of various garments, such as underwear, bras, shorts, pants, shirts, etc. In some embodiments, one or more of the layers 110, 130, 140, and/or 150 is sized for incorporation (e.g., cut, trimmed, singulated, or otherwise processed) into various garments before being stacked into the textile material 100. In some embodiments, the textile material 100 can be produced by an automated knitting machine that knits two or more of the layers 110, 130, 140, and/or 150 together in large sheets and/or rolls, such that multiple layers of, or even ever layer of, the textile material is manufactured as a single fabric.

Figure 2:
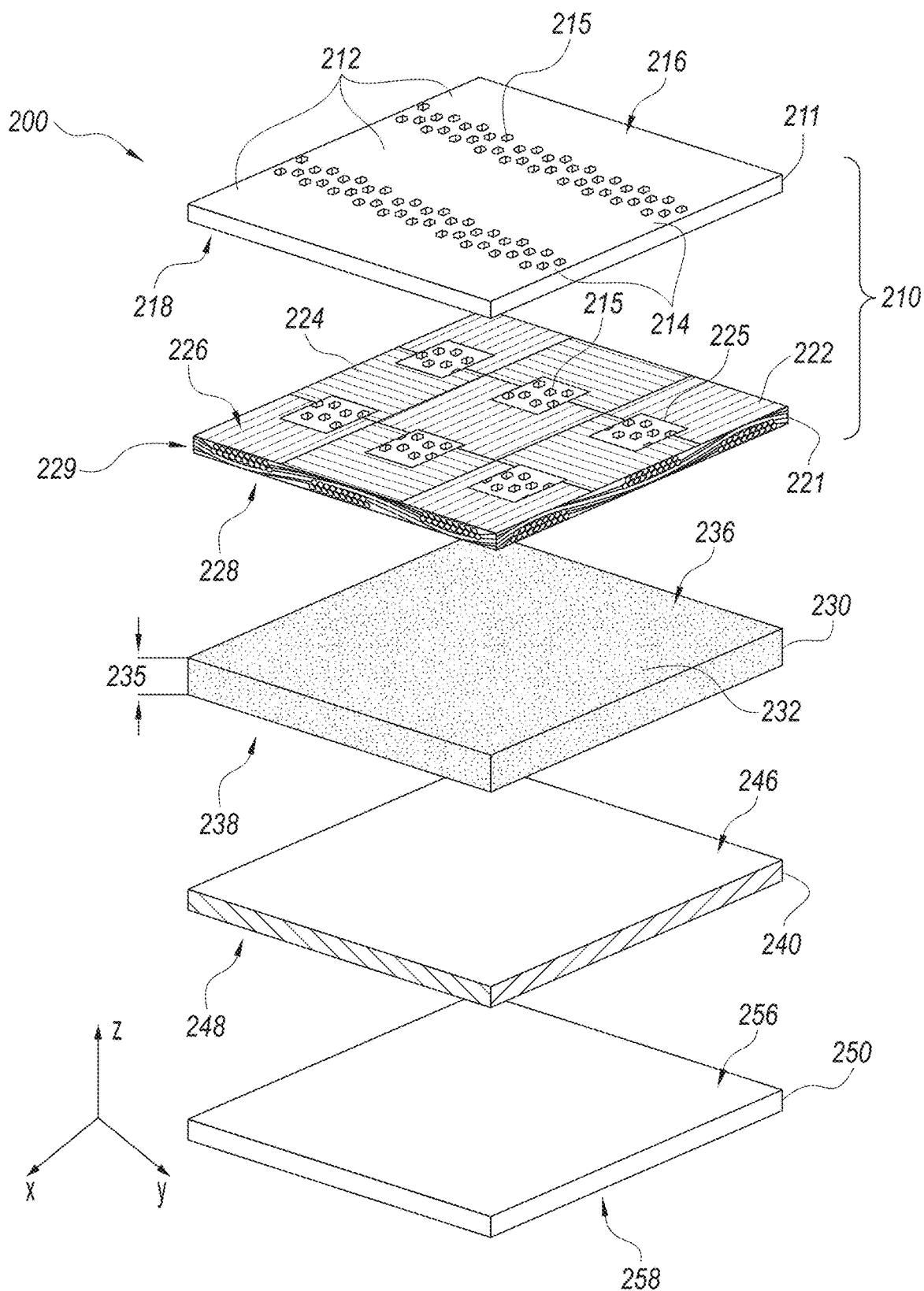
FIG. 2 is a cross-sectional exploded view showing the layers of a textile material in accordance with some embodiments of the present technology.

FIG. 2 is a cross-sectional exploded view illustrating details on various layers of a textile material 200 in accordance with some embodiments of the present technology. In the illustrated embodiment, the textile material includes a first layer 210, a second layer 230 beneath the first layer 210, a third layer 240 beneath the second layer 230, and a fourth layer 250 beneath the third layer 240. One of skill in the art, however, will understand that the other embodiments may involve orientations other than vertical. Rather, as noted above, the "upwards" in the z-direction may indicate a substantially, or partially, horizontal orientation, or both, while either the x-direction or y-direction may have components in the vertical direction of the garment. Accordingly, the orientation illustrated in FIGS. 2-5 and the vertical orientation used to describe the embodiments shown therein is for illustrative purposes only, and should not be read to limit the scope of the invention.

The textile material 200 includes a first layer 210 configured to contact and receive a liquid (e.g., a bodily fluid such as menstrual fluids, urine, pus, blood, etc.) from adjacent a user's skin when the textile material 200 is integrated into or worn with a garment. As described in more detail below, the first layer 210 disperses the liquid in the x-y plane (e.g., across a width and length of the first layer 210) while also pulling and/or allowing the liquid to flow downwards in the z-direction (e.g., through the thickness of the first layer 210) towards the second layer 230. The second layer 230 is an absorbent material that receives the liquid from the first layer 210 and contains the liquid within the second layer 230. In some embodiments, for example, the second layer 230 is made from a relatively highly hydrophilic material, such that when liquid is dispersed across the first layer 210 it is also drawn downwards in the z-direction and held in the second layer 230. Since the second layer 230 is removed from the skin-contacting surface by a distance (e.g., the thickness of the first layer 210), the skin-contacting surface can be dry to the touch while the textile material 200 contains a volume of liquid, thereby increasing a user's comfort while managing the liquid. The third layer 240 is a water-resistant layer that resists allowing the liquid to pass through it. Accordingly, the third layer 240 can resist any further flow of the liquid in the downward direction, aiding the second layer 230 in containing the liquid therein. The fourth layer 250 is a primarily decorative layer to allow the textile material 200 to be visually integrated into the garment. In some embodiments, for example, the fourth layer 250 can be the main fabric of the garment and/or cloth, thereby allowing the textile material 200 to be largely invisible to a viewer from the outside of the garment and/or cloth. Details on the construction and functionality of the layers, according to various embodiments of the invention, are provided below.

In some embodiments, the first layer 210 includes a first sublayer 211 and a second sublayer 221 beneath the first sublayer 211. The first and second sublayers 211, 221 can be a fabric having various knit-patterns that facilitate the dispersion of the liquid. For example, in some embodiments, the first and/or second sublayers 211, 221 include a mesh or open knit structure that allow the liquid to quickly pass through the thickness of the first layer 210. That is, as discussed in more detail below, the mesh knit structure can be positioned to facilitate dispersion of the liquid in the z-direction after (or concurrently with) dispersion in one or more x-y planes. In some embodiments, the knit pattern of the first and second sublayers 211, 221 can also aid in attaching the sublayers together (e.g., the first and second sublayers 211, 221 can be knit together). In other embodiments, various other means can be used to attach the first and second sublayers 211, 221 to form the first layer 210 (e.g., lamination, fabric glue, stitching, etc.).

In some embodiments, the first layer 210 can include any number of other sublayers configured to disperse the liquid in an x-y plane. Further, although described of sublayers of the first layer 210, it will be understood that the first sublayer 211 and second sublayer 221 can be described as a first layer and a second layer, and have been described together here has sublayers of the first layer 210 merely for convenience in illustrating the functionality of the first and second sublayers 211, 221.

In the illustrated embodiment, the first sublayer 211 includes a plurality of generally parallel first channels 212 and second channels 214 positioned side by side, an upper surface 216, and a lower surface 218. The first channels 212 provide a generally homogenous face on the upper surface 216 while the second channels 214 each include a plurality vertical channels 215 (e.g., mesh holes, openings, pores, etc.) providing a travel path from the upper surface 216 to the lower surface 218. For example, in one embodiment, the first channels 212 can be a knit structure having relatively small gaps between fibers, while the second channels 214 can be a mesh knit pattern providing the plurality of vertical channels 215. As a result, a liquid incident on the upper surface 216 will be resisted from moving vertically through the first channels 212 but will pass easily through the vertical channels 215 in the second channels 214.

Figure 3A:
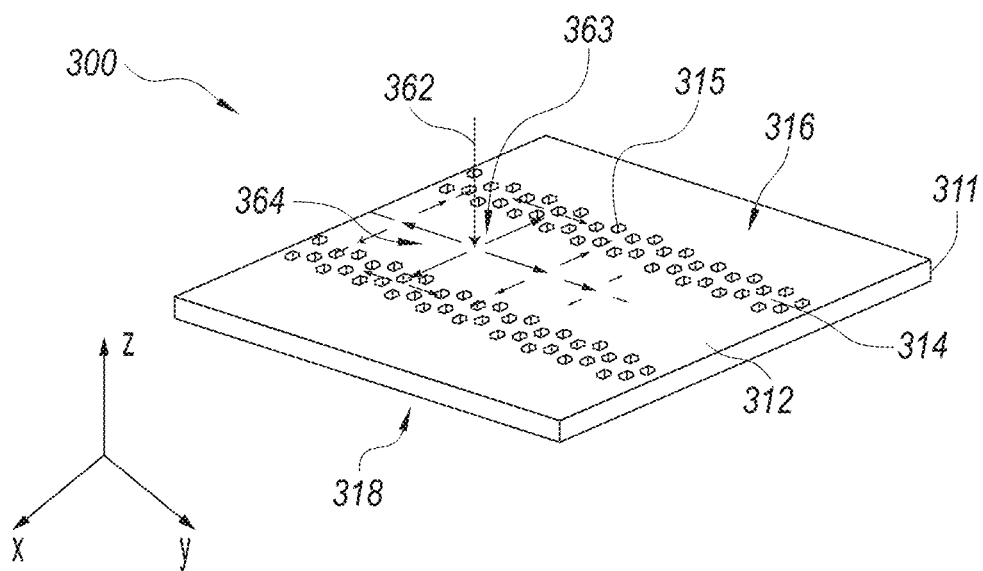
FIG. 3A is a cross-sectional isometric view of one layer of a textile material overlaid with a vector diagram indicating the flow of liquid incident on the layer in accordance with some embodiments of the present technology.

Further, the first sublayer 211 can be made from a water-repellent material (e.g., a hydrophobic material) such that the liquid incident on a first channel 212 on the upper surface 216 quickly spreads across the upper surface 216 towards the vertical channels 215 in the second channels 214 (see FIG. 3A). When the liquid reaches the pores in the second channels 214, the liquid can flow from the upper surface 216 towards the lower surface 218. As a result, the liquid can move quickly off the upper surface 216, leaving the upper surface 216 relatively dry to the touch. In some embodiments, the first sublayer 211 can be made from a polyester yarn, which will not absorb liquid into the fibers of the yarn. In some embodiments, for example, the first sublayer 211 can be Carat yarn available from Teijin and knit into the desired patterns.

The second sublayer 221 includes a fabric knit in a matrix (e.g., a grid pattern, a plurality of rows and columns, etc.) with fibers 222 in a first direction, fibers 224 in a second direction at least partially orthogonal to the first direction, an upper surface 226 configured to contact the lower surface 218 of the first sublayer 211, and a lower surface 228. In the illustrated embodiment, the second sublayer further includes a plurality of mesh sections 225, each having a plurality vertical channels 215 continuing from the first sublayer 211 therein. The vertical channels 215 in the mesh sections 225 extend from the upper surface 216 of the first sublayer 211 to the lower surface 228 of the second sublayer 221, while the vertical channels 215 outside of the mesh sections 225 extend only from the upper surface 216 of the first sublayer 211 to the lower surface 218 of the first sublayer 211. Liquid entering one of the vertical channels 215 extending completely through the first layer 210 is quickly dispersed to the second layer 230, while liquid entering one of the vertical channels 215 extending to the lower surface 218 of the first sublayer is incident on and dispersed in the second sublayer 221, as described in more detail below. In some embodiments, one or more of the vertical channels 215 in the mesh sections 225 extend from the upper surface 216 of the first sublayer 211 to an intermediate depth in the second sublayer 221. In these embodiments, liquid entering the one or more channels extending to an intermediate depth in the second sublayer 221 is quickly dispersed away from the upper surface 216 of the first sublayer 211 before being dispersed in the second sublayer 221, as described in more detail below. In some embodiments, one or more of the vertical channels 215 in the mesh sections 225 extend from the upper surface 216 of the first sublayer 211 to a region between the first sublayer 211 and the second sublayer 221. Similarly, in these embodiments, liquid entering the one or more vertical channels 215 extending only through the first sublayer 211 is quickly dispersed away from the upper surface 216 of the first sublayer 211 before being dispersed between the first sublayer 211 and the second sublayer 221.

In some embodiments, the mesh sections 225 are positioned in a grid pattern throughout the second sublayer 221. In the illustrated embodiment, each of the mesh sections 225 has a generally rectangular shape. In other embodiments, the mesh sections 225 can have various other suitable shapes (e.g., circular, ovular, triangular, one or more lines extending all the way across the second sublayer 221).

In the illustrated embodiment, the fibers 222 are oriented generally in the x-direction of an x-y plane while the fibers 224 are oriented generally orthogonally in the y-direction of the x-y plane. The fibers 222, 224 in the second sublayer 221 are a relatively hydrophilic and moisture wicking material that causes the liquid arriving from the plurality of vertical channels 215 in the first sublayer 211 to disperse in the x-y plane. More specifically, the fibers 222, 224 can be a material that uses the capillary effect to disperse in the generally in the direction of the fibers 222, 224. For example, if the liquid arrives at the upper surface 226 on fibers 222, the liquid will be dispersed in the x-direction. As described in more detail below, as the liquid is pulled along the direction of the fibers 222 or 224, some of the liquid will contact the generally orthogonal fibers 224 or 222, respectively, and be dispersed in the generally orthogonal direction. Further, some of the liquid will continue to disperse downwards towards the lower surface 228.

The vertical dispersion can be aided by increasing the number of mesh sections 225 and/or by a varying density of fibers 222, 224 in the second sublayer 221. For example, the amount of liquid that can be held and dispersed by the fibers 222, 224 is partially determined by the surface area of the fibers 222, 224, such that higher density regions can pull liquid from lower density regions. Accordingly, in some embodiments, the fibers 222, 224 are also stacked in the second sublayer 221 such that there are less fibers near the upper surface 226 than near the lower surface 228. For example, the sidewalls 229 of the cross section of the illustrated embodiment show that the second sublayer 221 includes an upper half of fibers 222, 224 stacked on top of a lower half of fibers 222, 224, where the upper half contains less fibers than the lower half (e.g., the upper half has a lower thread count than the lower half).

In some embodiments, the second sublayer 221 is also made from a polyester material such that the fibers 222, 224 do not absorb the liquid. In some embodiments, for example, the second sublayer 221 can be DeltaPeak yarn available from Teijin and knit into the matrix of fibers described above. In some embodiments, the second sublayer can have a hydrophilic rating between about 2 millimeter per second (mmps) spreading speed to about 8 mmps spreading speed, from about 4 mmps spreading speed to about 6.6 mmps spreading speed, or of about 5.5 mmps spreading speed.

The second layer 230 includes an absorbent material 232, a thickness 235, an upper surface 236, and a lower surface 238. When the textile material 200 is constructed, upper surface 236 of the second layer 230 can be in contact with the lower surface 228 of the second sublayer 221 of the first layer 210 such that the second layer 230 can absorb the liquid from the lower surface 228. In some embodiments, the second layer 230 is attached to the first layer through various stitching patterns (e.g., sewn together at the edges, sewn in a grid pattern, or various other suitable patterns). The position of the absorbent material 232 beneath the first layer 210 increases the transfer of liquid from the lower surface 228 down to the second layer 230. This transfer moves the liquid further away from the upper surface 216 of the first sublayer 211, which significantly improves comfort to a user of the textile material 200.

In some embodiments, the absorbent material 232 can be a polyester-based fabric that absorbs liquids between the fibers rather than into the fibers themselves. For example, in various embodiments, the absorbent material 232 can be a polyester-based fabric available from Labtex China and/or Labtex Taiwan. As discussed above, the capacity of a polyester material can be increased by providing more fiber surface area to hold the liquid. Accordingly, the absorbent material 232 can be a polyester fabric with relatively small fibers knit into a double-interlock weave, and therefore more surface area per sheet. For example, in some embodiments, the absorbent material 232 is a polyester fabric with a denier of between about 40D to about 80D, of about 50D, or of about 75D. In some embodiments, the absorbent material 232 can be a fabric that also absorbs liquids into the fibers themselves (e.g., employing cotton or other absorbent fibers). Because the liquids are absorbed into the fibers themselves, the absorbent material 232 can very effectively trap the liquid absorbed. However, such fabrics may also take longer to dry because the liquid is trapped in the fibers of the fabric itself.

The capacity of the absorbent material 232 is affected by the thickness 235 of the absorbent material 232, and can be calculated as being able to absorb about at least three times the weight of the absorbent material 232 in water weight. In some embodiments, for example, the thickness 235 can be about 0.5 millimeters (mm) to give the second layer 230 a weight of between about 90 grams per square meter (gsm), thereby resulting in an absorbing capacity of at least about 270 gsm. In some embodiments, the thickness 235 can be about 0.72 mm to give the second layer 230 a weight of about 180 gsm, thereby resulting in an absorbing capacity of at least about 540 gsm. In various other embodiments, the thickness 235 can range from about 0.035 mm to about 1.15 mm resulting in various other weights and absorbing capacities.

The third layer 240 is a leak resistant material having an upper surface 246 and lower surface 248. The upper surface 246 is attached to the lower surface 238 of the second layer 230 to impede (e.g., reflect, block, stop, slow down, etc.) liquids from leaking from the lower surface 238. In some embodiments, the third layer 240 is attached to the second layer 230 through a lamination process. In some embodiments, the lamination includes intermediate lamination materials between the upper surface 246 of the third layer 240 and the lower surface 238 of the second layer 230. In other embodiments, the upper surface 246 of the third layer 240 can be laminated directly onto the lower surface 238 of the second layer 230 to reduce weight, thickness, and the cost of the textile material 200.

In some embodiments, the third layer 240 can be chosen based on the water resistance of the material. For example, in some embodiments, the third layer 240 can be made from a polyurethane material. In some embodiments, the third layer 240 can also be chosen based on breathability, stretchability, rigidity, and/or the hand-feel of the material. In some embodiments, for example, the third layer 240 can be a C48 non-porous hydrophilic membrane, such as various fabrics available from GFun in Taiwan, which can have a water resistance rating of 15,000 mm and a Moisture Vapor Permeability (MVP) rating of 150,000 gsm in 24 hours, while being a stretchable and flexible fabric.

The fourth layer 250 is primarily an aesthetic fabric chosen to integrate the textile material 200 into the remainder of the garment. That is, the fourth layer 250 is chosen primarily for the look, feel, and performance of the fabric, for example with respect to how it fits on the body of the user. For example, in some embodiments, the fourth layer 250 can be one or more of various fabrics available from Best Pacific Textile Co. In some embodiments, however, an upper surface 256 of the fourth layer 250 can also be coated with a durable water repellant finish that further prevents any liquids from reaching a lower surface 258.

In some embodiments, each of the layers 210-250 can be chemically treated to further enhance the functionality of the layers. For example, in some embodiments, all, or a few of, the layers 210-250 can be at least partially treated with an odor control agent and/or antimicrobial compound (e.g., a silver containing compound such as HeiQ® Pure SPQR). In some embodiments, all, or a few of, the layers 210-250 can be at least partially treated with a non-anti-microbial odor controlling agent. In some embodiments, all, or a few of, the layers 210-250 can be at least partially treated with an agent that provides a soft and/or cool touch, increases moisture wicking and/or encourages stain release.

FIG. 3A is a cross-sectional isometric view of a first sublayer 311 of a textile material 300 overlaid with a vector diagram indicating the flow of liquid incident on the first sublayer 311 in accordance with some embodiments of the present technology. In the vector diagram, volumetric flow of a liquid in a spatial location is generally indicated by the size of the vector arrow at the spatial location. For example, a first arrow having a first length indicates a larger volume of low than a second arrow having a second length shorter than the first arrow.

In the illustrated embodiment, the first sublayer 311 is generally similar in structure to the first sublayer 211 (FIG. 2). For example, the first sublayer 311 includes a plurality of first horizontal channels 312, a plurality second horizontal channels 314 having a plurality of vertical channels 315, an upper surface 316, and a lower surface 318.

As illustrated in FIG. 3A, a first flow 362 of the liquid is incident on the upper surface 316 of the first sublayer 311 and contacts one of the first channels 312 at a contact point 363. The first flow 362 is then dispersed circumferentially outwards from the contact point 363 in an x-y plane in a second flow 364. The farther from the contact point 363 on the x-y plane the dispersed liquid gets, the more dissipated the second flow 364 becomes. Further, as the second flow 364 spreads in the x-direction, the second flow 364 eventually reaches the second channels 314 of the first sublayer 311. When the liquid reaches the second channels 314 it disperses rapidly along the channels in the y-direction as it is pulled into each of the vertical channels 315. Here, some of the liquid in the second flow 364 travels from the upper surface 316 of the first sublayer 311 towards the lower surface 318, while some of the liquid in the second flow 364 continues to be dispersed in the x-y plane. As the liquid from the second flow 364 reaches the lower surface 318, some becomes incident on an upper surface 326 of a second sublayer 321 (FIG. 3B), while some continues through the vertical channels 315 extending through the first layer.

Figure 3B:
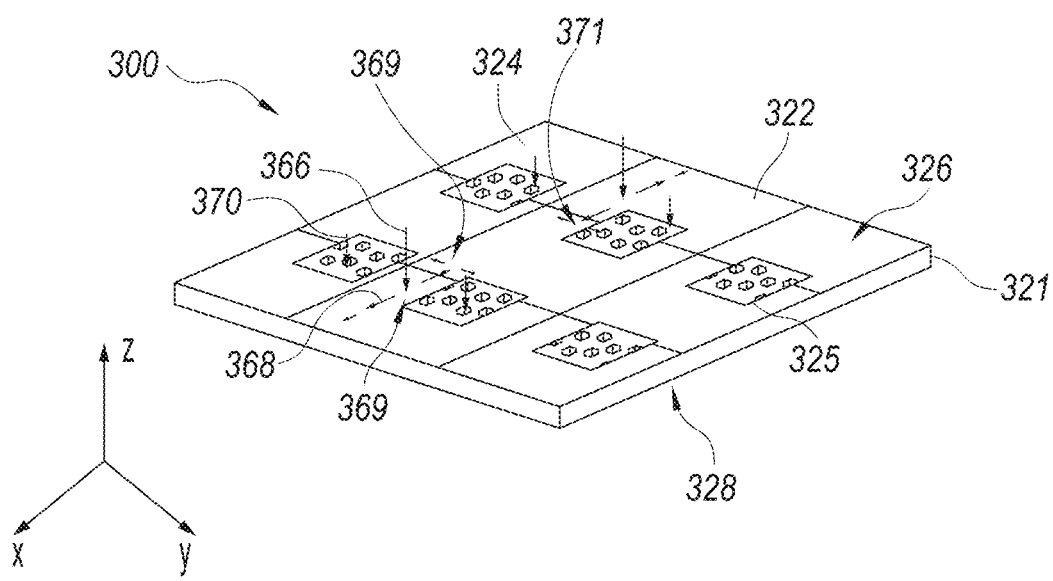
FIG. 3B is a cross-sectional isometric view of a second layer of a textile material overlaid with a vector diagram indicating the flow of liquid incident on the layer in accordance with some embodiments of the present technology.

FIG. 3B is a cross-sectional isometric view of the second sublayer 321 of the textile material 300 overlaid with a vector diagram indicating the flow of a liquid incident on the second sublayer 321 in accordance with some embodiments of the present technology. In the illustrated embodiment, the second sublayer 321 is generally similar in structure to the second sublayer 221 (FIG. 2). For example, the second sublayer 321 includes a grid of fibers (partially shown) oriented in the x and y-directions, mesh sections 325 having the vertical channels 315, the upper surface 326, and a lower surface 328.

As a result of the dispersion in the first sublayer 311 discussed above with respect to FIG. 3A, the liquid arrives at the second sublayer 321 in a third flow 366 and a fifth flow 370. The liquid arriving at the second sublayer 321 in the third flow 366 is incident on a plurality of contact points 367 on the upper surface 326. The third flow 366 is then dispersed into a fourth flow 368 in the x-y plane in either the x-direction or the y-direction, according to the orientation of the fibers (see FIG. 2) at the contact points 367. For example, liquid in the third flow 366 contacting fibers oriented in the x-direction will be further dispersed in the x-direction. As the fourth flow 368 travels in the x-y plane, the fourth flow 368 is also drawn further downwards towards the lower surface 328 by the availability of space between fibers closer to the lower surface 328. Meanwhile, the liquid arriving at the second sublayer 321 in the fifth flow 370 is contained in the vertical channels 315 and continues to move downwards through the vertical channels 315. Accordingly, liquid in the fifth flow 370 moves quickly from the upper surface 316 of the first sublayer 311 (FIG. 3A) to the lower surface 328 of the second sublayer 321.

As further illustrated in FIG. 3B, liquid in the fourth flow 368 can initially be drawn in a first direction by a first set of fibers, contact a second set of fibers at a secondary contact point 369, and then be drawn in a second direction by the second set of fibers. For example, the liquid in the third flow 366 can contact fibers oriented in the x-direction such that the liquid in the fourth flow is initially pulled in the x-direction. The liquid in the fourth flow 368 can then contact fibers oriented in the y-direction at a secondary contact point 369 to be pulled in the y-direction. In some embodiments, the liquid in the fourth flow 368 is incident on one or more of the mesh sections 325, for example as shown at third contact point 371. At the third contact point 371, liquid in the fourth flow 368 can merge into the fifth flow and disperse directly downwards through one or more of the vertical channels 315. In other embodiments, each of the mesh sections 225 can be isolated from the remainder of the second sublayer 321, such that liquid incident on the third contact point 371 does not merge with the fifth flow. The result of the two layers of dispersion is shown by the vector diagram overlays in FIG. 4

Figure 4:
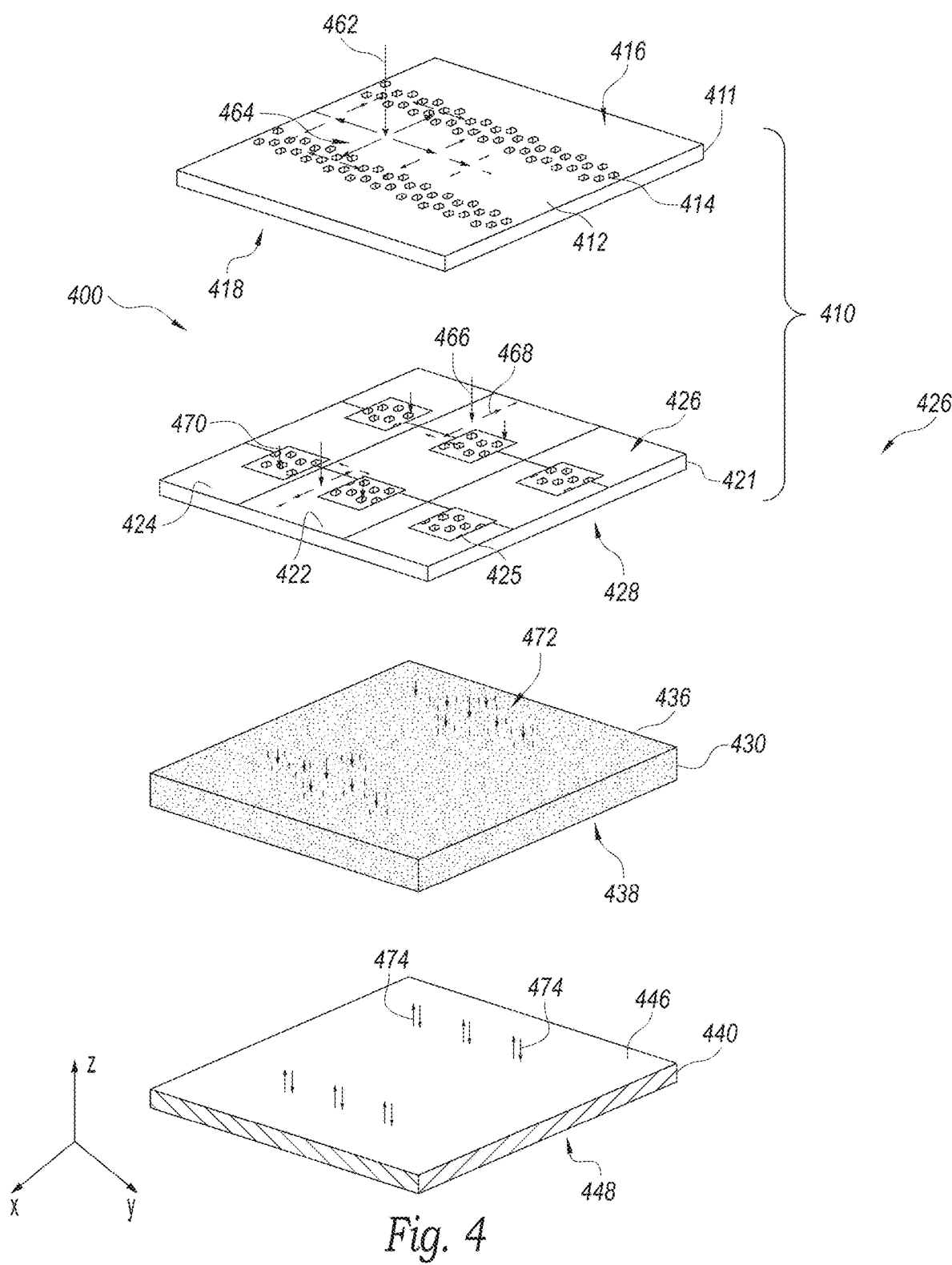
FIG. 4 is a cross-sectional exploded view of a textile material overlaid with a vector diagram indicating the flow of liquid through the textile material in accordance with some embodiments of the present technology.

FIG. 4 is a cross-sectional exploded view of a textile material 400 overlaid with a vector diagram indicating the flow of liquid through the textile material 400 in accordance with some embodiments of the present technology. In the illustrated embodiment, the textile material 400 is generally similar in structure to the textile material 200 discussed with respect to FIG. 2 above. For example, the textile material 400 includes a first layer 410 having a first sublayer 411 and a second sublayer 421, a second layer 430, and a third layer 440.

FIG. 4 illustrates the dispersed volume of liquid as it is absorbed into the textile material through a series of flows dictated by the layers in the textile material 400. For example, a first flow 462 arrives at an upper surface 416 of the first sublayer 411 and is dispersed in a second flow 464 in a first x-y plane. As the second flow 464 reaches vertical channels 415 in the second channels 414, the second flow 464 can travel through the first sublayer 411 into a third flow 466 and a fifth flow 470. The third flow 466 is then incident on an upper surface 426 of the second sublayer 421 and is dispersed through a fourth flow 468. The fourth flow 468 disperses the liquid in a second x-y plane while also drawing the liquid to the lower surface 428 of the second sublayer 421. As the fourth flow is dispersed, liquid in the fifth flow 470 moves continues to flow directly in the vertical direction towards the lower surface 428 of the second layer 421. When liquid in the fourth flow 468 and the fifth flow 470 reach the lower surface 428, it contacts the upper surface 436 of the second layer 430 and is pulled into the second layer 430 through a sixth flow 472. Because the second layer is relatively absorbent compared to the other layers, the sixth flow 472 is typically a terminal flow into the second layer 430. In some instances, however, portions of the second layer 430 can become saturated and some of the liquid can leak from the lower surface 438 of the second layer 430 into a seventh flow 474. The seventh flow 474 contacts and is reflected by the third layer 440 back into the second layer 430, thereby maintaining the second layer 430 as the terminus of the liquid flows.

Accordingly, the liquid can be transported and dispersed from a skin contacting surface (the upper surface 416 of the first sublayer 411) to an interior layer (the second layer 430) for storage. By holding the liquid in an x-y plane separated from the skin contacting surface by some distance, the textile material 400 can increase user comfort while containing the liquid. Further, because the seventh flow 474 is redirected into the second layer, no (or almost no) liquid is communicated to an exterior-facing surface (e.g., the lower surface 448 of the third layer 440, the lower surface 258 of the fourth layer 250 (FIG. 2), etc.). As a result, the liquid is discretely contained in the textile material 400.

Further, through the combination of materials and features discussed above, the textile material 400 is able to quickly disperse the liquid from the skin contacting surface to the interior layer for storage. For example, in some embodiments, a small amount (e.g., 2 ml, 5 ml, 10 ml, or 25 ml) of a liquid incident on the skin contacting surface can be substantially dispersed (e.g., at least 90% dispersed, at least 80% dispersed, at least two-thirds dispersed, or more than half dispersed) away from the skin contacting surface very quickly (e.g., within 5 seconds, within 10 seconds, or within 30 seconds). In some embodiments, the textile material 400 can substantially disperse small amounts of any liquid (e.g., water, urine, blood, menstrual fluid, breast milk, or any other liquid) in a similarly short amount of time (e.g., within 5 seconds, within 10 seconds, or within 30 seconds).

Figure 5:
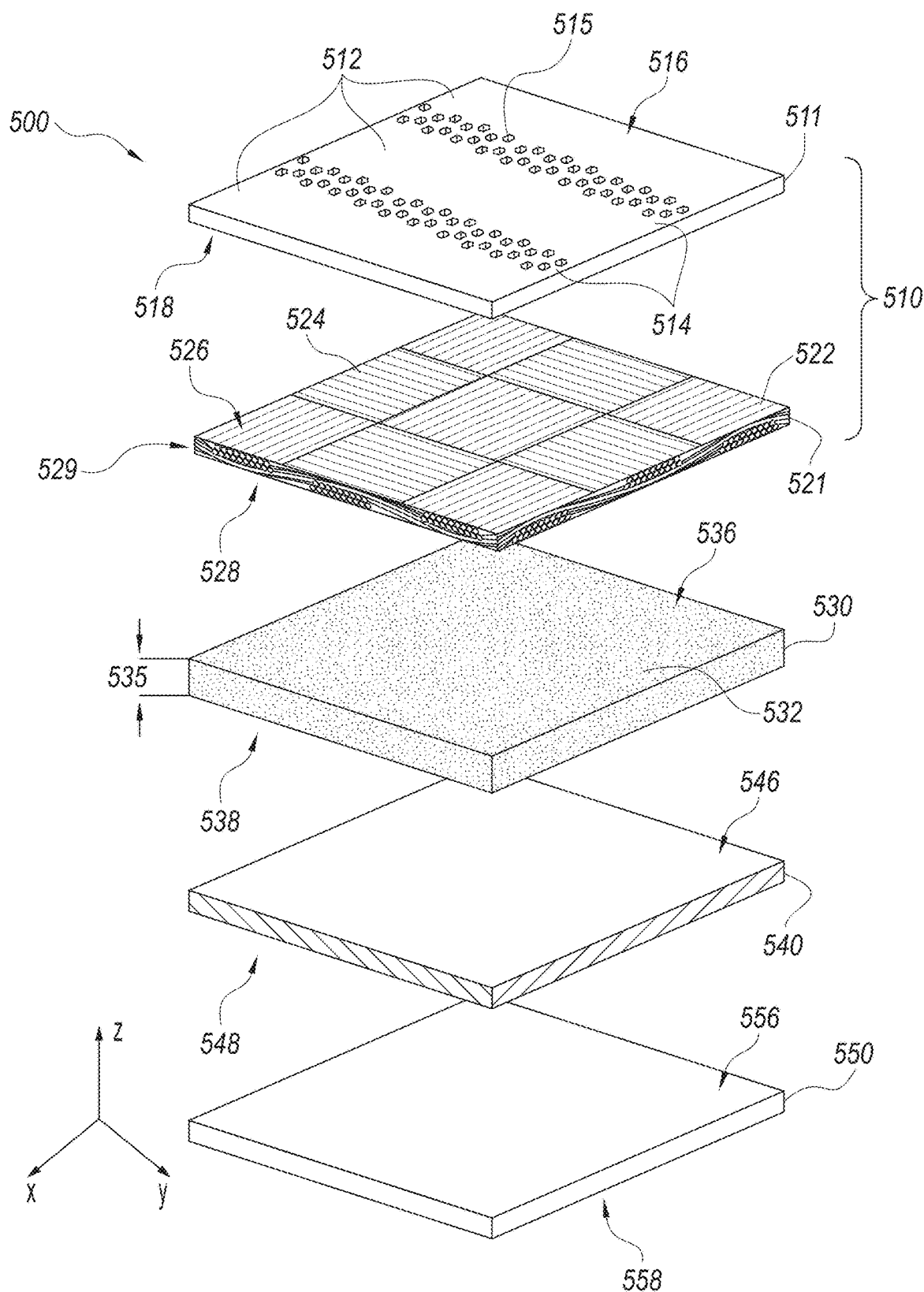
FIG. 5 is a cross-sectional isometric view of another stack of layers in accordance with some embodiments of the present technology.

FIG. 5 is a cross-sectional exploded view of a textile material 500 in accordance with another embodiment of the present technology. In the illustrated embodiment, the textile material 500 is generally similar in structure to the textile material 200 and 400 discussed above with respect to FIGS. 2 and 4. However, in the illustrated embodiment, the second sublayer 521 does not include any mesh sections. Instead, all of the liquid arriving from the first sublayer 511 is incident on the upper surface 526 of the second sublayer 521 and therefore dispersed in the x-y plane in the second sublayer 521. As a result, the liquid arriving at the second layer 530 can be more evenly dispersed and therefore more spread. However, because there are no vertical channels 515 in the second sublayer 521, the liquid can take longer to disperse in the downwards direction, causing a delay before the upper surface 516 of the first sublayer 511 (e.g., the skin-facing surface) is generally dry.

Figure 6:
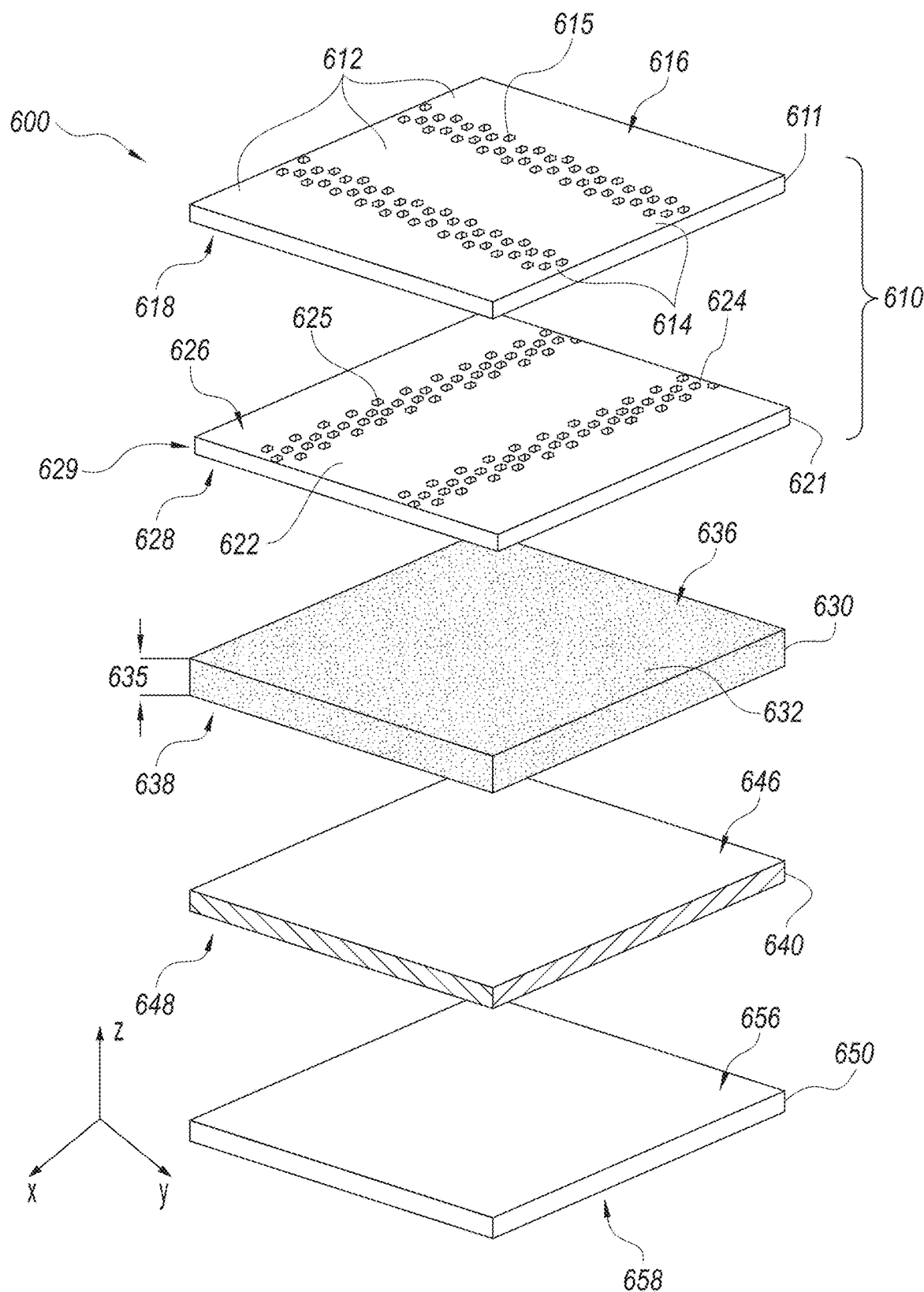
FIG. 6 is an isometric front view of a garment incorporating the textile material in accordance with some embodiments of the present technology.

FIG. 6 is a cross-sectional exploded view of a textile material 600 in accordance with another embodiment of the present technology. In the illustrated embodiment, the textile material 600 is generally similar in structure to the textile material 200 and 400 discussed above with respect to FIGS. 2 and 4. However, in the illustrated embodiment, the second sublayer 621 of the first layer 610 is a duplicate of the first sublayer 611, oriented in a cross-hatched direction. That is, the first layer 610 contains two sublayers of a generally hydrophobic material, each having generally parallel first channels 612, 622 and second channels 614, 624. Accordingly, a liquid incident on the first layer 610 is quickly dispersed in the x-y plane by each of the first and second sublayers 611, 621. Because the liquid primarily (or only) flows vertically through the vertical channels 615, 625, the liquid primarily arrives at the upper surface 636 of the second layer 630 in lines corresponding to the vertical channels 625 of the second sublayer 621. However, the first and second sublayers 611, 621 also spread the liquid further in the x-y plane in the first layer 610 (e.g., compared to the first layer 510 discussed above with respect to FIG. 5). Accordingly, although the liquid arrives primarily at the arrives at the upper surface 636 of the second layer 630 in lines corresponding to the vertical channels 625 of the second sublayer 621, the liquid is also spread enough in the x-y plane that the corresponding portions of the second layer 630 are not quickly saturated.

It will be understood that in further embodiments of the present technology, the first layer of the textile material can include any number of sublayers with various combinations of the features discussed above. Purely by way of example, in some embodiments, the first layer includes two sublayers with channels of hydrophobic material and one sublayer with a grid of hydrophilic material. In these embodiments, the two sublayers with channels of hydrophobic material can be stacked on top of the sublayer with a grid of hydrophilic material such that the upper two layers quickly disperse a liquid away from the uppermost surface while dispersing the liquid in the x-y plane, before the lower layer more fully disperses the liquid in the x-y plane while dispersing the liquid further away from the uppermost surface. As another example, in some embodiments, the first layer can include only a single sublayer, with any of the features discussed above (e.g., the first sublayer 211 (FIG. 2), the second sublayer 221 (FIG. 2), the second sublayer 521 (FIG. 5), or any other suitable configuration).

Figure 7:
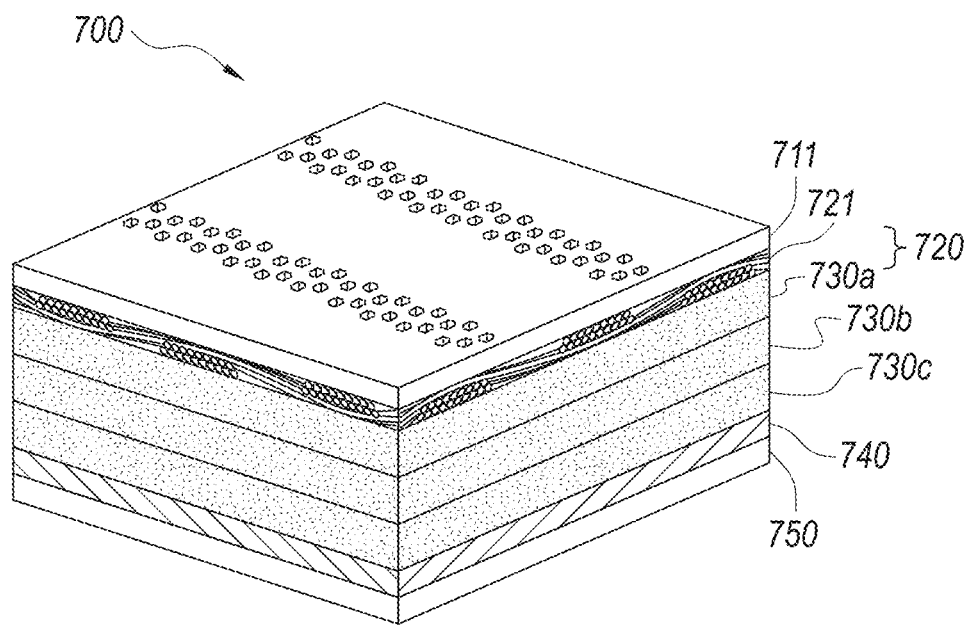
FIG. 7 is a cross-sectional isometric view of a textile material in accordance with some embodiments of the present technology.

FIG. 7 is a cross-sectional isometric view of a textile material 700 in accordance with another embodiment of the present technology. The textile material 700 is generally similar in structure to the textile material 200 disclosed above with respect to FIG. 2. In the illustrated embodiment, however, the textile material 700 includes three absorbent layers 730a-c corresponding to duplicates of the second layer 230 of FIG. 2. Including multiple absorbent layers 730a-c in the textile material 700 increases the absorbing capacity of the textile material 700, allowing it to be used in settings likely to require a larger holding capacity. Purely by way of example, the textile material 700 can be incorporated into a garment (e.g., underwear) to discreetly contain accidental urination by the wearer, which may require the ability to contain a relatively large volume of liquid. In various other embodiments, any number of absorbent layers 730a-N can be used in the textile material to absorb and hold liquids. It will be understood that, in general, the more absorbent layers 730a-N that are used, the thicker the textile material will become, and therefore the more the garment or cloth will noticeably depart from a traditional fabric. Conversely, the fewer absorbent layers 730a-N, the thinner the textile material 700 will be, and therefore the closer the garment or cloth will feel like a traditional fabric. In various embodiments, the total thickness of the textile material can range from about 0.8 mm to about 5 mm, from about 1.3 mm to about 2.7 mm, can be about 1.5 mm, or can be about 2.4 mm.

Figure 8:
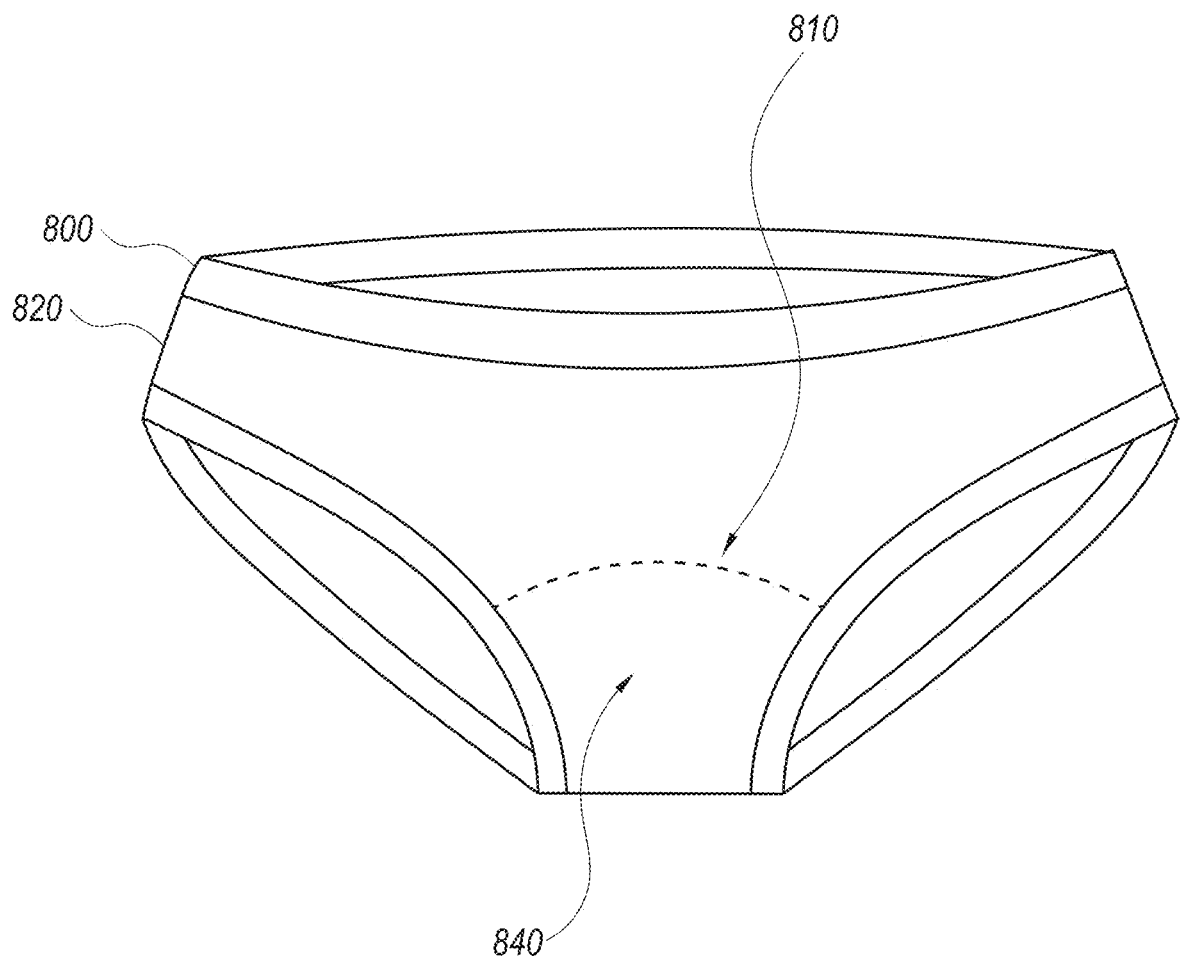
FIG. 8 is an isometric front view of a garment in accordance with some embodiments of the present technology.

In some embodiments, the absorbent layers 730a-c can have a generally equal fiber density and thickness. In various other embodiments, the absorbent layers 730a-c can have a generally equal density but a different thickness (and therefore different weights), a different density but a generally equal thickness, or a different density and different thickness. In some embodiments, the absorbent layers 730a-c can increase in density deeper into the textile material such that absorbent layer 730c has a higher density than absorbent layer 730a. In these embodiments, the majority of the liquid contained in absorbent layers 730a-c when they are saturated is therefore contained farther from the skin-contacting surface of the textile material, which can result in greater comfort for the user. FIG. 8 is an isometric front view of a garment 800 incorporating the textile material 810 in accordance with some embodiments of the present technology. In the illustrated embodiment, the garment 800 is a pair of underwear made from fabric 820 and that has the textile material 810 integrated into a crotch region 840 of the garment 800. In the illustrated embodiment, the fourth layer (e.g., the outermost layer) of the textile material 810 can include the fabric 820, thereby visually blending the textile material 810 into the remainder of the garment 800. In some embodiments, the fourth layer can include a second fabric visually paired with the fabric 820 for an aesthetic look. In some embodiments, the textile material 810 can be integrated into more regions of the garment 800. In other embodiments, the textile material 810 can be integrated into a smaller portion of the crotch region 840 of the garment 800. In still other embodiments, the textile material 810 can be an independent element, such as a pad, that can be worn between the garment 800 and the body of the user.

EXAMPLES

Various examples of aspects of the subject technology described above with reference to FIGS. 1-8 are provided as numbered clauses (1, 2, 3, etc.) for convenience. These are provided as examples and do not limit the subject technology.

1. A textile material for managing a bodily fluid, the textile material comprising:
    a first layer having an inner surface and an outer surface, wherein the first layer is configured to draw the bodily fluid through a thickness of the first layer from the inner surface to the outer surface while dispersing the bodily fluid laterally across the first layer; and
    a second layer in contact with the outer surface of the first layer, wherein the second layer is configured to pull the bodily fluid away from the outer surface and hold the bodily fluid in the second layer; and a third layer opposite the second layer from the first layer, wherein the third layer is configured to confine the bodily fluid within the second layer.

2. The textile material of clause 1 wherein the first layer comprises:
   a hydrophobic inner material, the inner material including a plurality of horizontal channels and a plurality of vertical channels arranged along each of the plurality of horizontal channels, wherein the inner material is configured to move the bodily fluid vertically away from the inner surface; and
   a hydrophilic outer material, the outer material including a generally horizontal grid of hydrophilic fibers configured to cause the bodily fluid to disperse laterally through the grid and draw the bodily fluid towards the outer surface.

3. The textile material of clause 2 wherein:
   the grid of hydrophilic fibers comprises a plurality of horizontal rows and columns,
   each row and column has a plurality of fibers in the row or column, and
   each row and column has a first thread count on an upper half of the row and column and a second thread count higher than the first thread count on a lower half of the row and column.

4. The textile material of clauses 2-3 wherein one or more of the vertical channels of the inner material extends at least partially through the outer material towards the outer surface.

5. The textile material of clauses 1-4 wherein the second layer includes a first sublayer having a first material density and a second sublayer having a second material density higher than the first material density.

6. The textile material of clauses 1-5 wherein the first layer comprises:
   a hydrophobic inner material, the inner material including a plurality of first horizontal channels and a plurality of vertical channels arranged along each of the plurality of horizontal channels, wherein the inner material is configured to move the bodily fluid vertically away from the inner surface; and
   a hydrophobic outer material, the outer material including a plurality of second horizontal channels at least partially orthogonal to the first horizontal channels and a plurality of vertical channels arranged along each of the plurality of horizontal channels, wherein the outer material is configured to move the bodily fluid vertically towards the outer surface.

7. The textile material of clauses 1-5 wherein the first layer comprises:
   a hydrophobic inner material, the inner material including a plurality of first horizontal channels and a plurality of vertical channels arranged along each of the plurality of horizontal channels, wherein the inner material is configured to move the bodily fluid vertically away from the inner surface;
   a hydrophobic middle material, the middle material including a plurality of second horizontal channels at least partially orthogonal to the first horizontal channels and a plurality of vertical channels arranged along each of the plurality of horizontal channels, wherein the middle material is configured to move the bodily fluid vertically towards the outer surface; and
   a hydrophilic outer material, the outer material including a generally horizontal grid of hydrophilic fibers configured to cause the bodily fluid to disperse laterally through the grid and draw the bodily fluid towards the outer surface.

8. The textile material of clauses 1-7 wherein the third layer includes a non-porous hydrophilic membrane configured to block flow of the bodily fluid through the membrane.

9. The textile material of clauses 1-8 wherein the liquid has a volume, and wherein the first layer is configured to draw at least 90% of the volume of the liquid through the first layer to the second layer within five seconds of the volume of the liquid contacting the inner surface of the first layer.

10. The textile material of clauses 1-9, further comprising a fourth layer opposite the third layer from the second layer, the fourth layer including an interior surface and an exterior surface opposite the interior surface, wherein the fourth layer includes a durable water-repellant finish on the interior surface configured to at least partially block the bodily fluid from flowing through the fourth layer.

11. A garment configured to be used in containing a liquid expelled from a body, the garment comprising:
    a first portion positioned in the garment to receive the liquid, the first portion including:
      a first layer configured to contact the body, the first layer including a plurality of channels configured to allow the liquid to flow in a first plane towards a plurality of pores that allow the liquid to flow in a direction generally orthogonal to the first plane;
      a second layer opposite the first layer from the body, the second layer including a matrix of hydrophilic fibers configured to disperse the liquid in a second plane generally parallel with the first plane and at least one section generally corresponding to at least one pore of the plurality of pores, the at least one pore extending through the section of the second layer;
      a third layer opposite the second layer from the first layer, the third layer including a hydrophilic material configured to absorb the liquid from the second layer and hold the liquid in the third layer; and
      a fourth layer opposite the third layer from the second layer, the fourth layer including a moisture-resistant material configured to at least partially block the liquid from moving through the fourth layer and;
    a second portion attached to the first portion.

12. The garment of clause 11 wherein the garment is a pair of underwear, and wherein the first portion includes at least a crotch portion of the underwear.

13. The garment of clauses 11-12 wherein the garment is a bra and wherein the first portion includes at least one cup of the bra.

14. The garment of clauses 11-13 wherein the garment is a pair of compression shorts, and wherein the first portion includes at least a crotch of the compression shorts.

15. A textile material for managing a bodily fluid comprising:
    a first layer configured to disperse the bodily fluid arriving at an inner surface of the first layer, wherein the first layer includes—
      a first material having a plurality of generally horizontal hydrophobic channels and a plurality of generally vertical channels, wherein the generally horizontal channels are configured disperse the bodily fluid towards the generally vertical channels, and wherein the plurality of vertical channels are configured to draw the bodily fluid vertically away from the inner surface;

a second material in contact with the first material opposite the inner surface, the second material having a matrix of hydrophilic fibers configured to receive the bodily fluid from the generally vertical channels, disperse the bodily fluid in a horizontal plane, and draw the bodily fluid towards an outer surface of the first layer, wherein at least one of the vertical channels extends from the inner surface to the outer surface through the second material; and a second layer in contact with the outer surface, the second layer comprising a hydrophilic material configured to receive the bodily fluid from the first layer and contain the bodily fluid in the second layer; and a third layer opposite the second layer from the first layer, the third layer including a moisture-resistant material in contact with the second layer, wherein the moisture-resistant material is configured to block the bodily fluid from flowing through the third layer.

16. The textile material of clause 15 wherein the hydrophilic material in the second layer is a first hydrophilic material in a first sublayer, and wherein the second layer further comprises a second hydrophilic material in a second sublayer.

17. The textile material of clause 16 wherein the first hydrophilic layer has a first material density and the second hydrophilic material has a second material density higher than the first material density.

18. The textile material of clauses 15-17 wherein the third layer is laminated directly onto the second layer.

19. The textile material of clauses 15-19, further comprising a fourth layer opposite the third layer from the second layer, the fourth layer including an interior surface and an exterior surface opposite the interior surface, wherein the fourth layer includes a durable water repellant finish on the interior surface configured to at least partially block the liquid from flowing through the fourth layer.

20. The textile material of clauses 15-20 wherein the matrix of hydrophilic fibers has a first thread count on an upper half of the second material and a second thread count higher than the first thread count on a lower half of the second material.

From the foregoing, it will be appreciated that specific embodiments of the technology have been described herein for purposes of illustration, but well-known structures and functions have not been shown or described in detail to avoid unnecessarily obscuring the description of the embodiments of the technology. To the extent any material incorporated herein by reference conflicts with the present disclosure, the present disclosure controls. Where the context permits, singular or plural terms may also include the plural or singular term, respectively. Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Furthermore, as used herein, the phrase "and/or" as in "A and/or B" refers to A alone, B alone, and both A and B. Additionally, the terms "comprising," "including," "having," and "with" are used throughout to mean including at least the recited feature(s) such that any greater number of the same features and/or additional types of other features are not precluded.

From the foregoing, it will also be appreciated that various modifications may be made without deviating from the disclosure or the technology. For example, one of ordinary skill in the art will understand that various components of the technology can be further divided into subcomponents, or that various components and functions of the technology may be combined and integrated. In addition, certain aspects of the technology described in the context of particular embodiments may also be combined or eliminated in other embodiments. Furthermore, although advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A textile material for managing a bodily fluid, the textile material comprising:
   a first layer having an inner surface and an outer surface, wherein the first layer is configured to draw the bodily fluid through a thickness of the first layer from the inner surface to the outer surface while dispersing the bodily fluid laterally across the first layer, and wherein the first layer comprises:
      a hydrophobic inner material, the inner material including a first knit pattern having a plurality of horizontal channels and a plurality of vertical channels arranged along each of the plurality of horizontal channels, wherein the hydrophobic inner material is configured to move the bodily fluid vertically away from the inner surface; and
      a hydrophilic outer material, the outer material including a generally horizontal knitted grid of hydrophilic fibers configured to cause the bodily fluid to disperse laterally through the knitted grid and draw the bodily fluid towards the outer surface; and
   a second layer in contact with the outer surface of the first layer, wherein the second layer is configured to pull the bodily fluid away from the outer surface and hold the bodily fluid in the second layer; and
   a third layer opposite the second layer from the first layer, wherein the third layer is configured to confine the bodily fluid within the second layer.

2. The textile material of claim 1 wherein:
   the knitted grid of hydrophilic fibers comprises a plurality of horizontal rows and columns,
   each row and column has a plurality of fibers in the row or column, and
   each row and column is knitted to have a first thread count on an upper half of the row and column and a second thread count higher than the first thread count on a lower half of the row and column.

3. The textile material of claim 1 wherein a first subset of one or more of the vertical channels of the inner material extends at least partially through the outer material towards the outer surface, and wherein a second subset one or more of the vertical channels of the inner material extends from the inner surface to an intermediate surface between the hydrophobic inner material and the hydrophilic outer material.

4. The textile material of claim 3 wherein the second layer includes a first sublayer having a first material density and a second sublayer having a second material density higher than the first material density.

5. The textile material of claim 1 wherein the first layer comprises:
a hydrophobic inner material, the inner material including a plurality of first horizontal channels and a plurality of vertical channels arranged along each of the plurality of horizontal channels, wherein the inner material is configured to move the bodily fluid vertically away from the inner surface;
a hydrophobic middle material, the middle material including a plurality of second horizontal channels at least partially orthogonal to the first horizontal channels and a plurality of vertical channels arranged along each of the plurality of horizontal channels, wherein the middle material is configured to move the bodily fluid vertically towards the outer surface; and
a hydrophilic outer material, the outer material including a generally horizontal grid of hydrophilic fibers configured to cause the bodily fluid to disperse laterally through the grid and draw the bodily fluid towards the outer surface.

6. The textile material of claim 1 wherein the third layer includes a non-porous hydrophilic membrane configured to block flow of the bodily fluid through the membrane.

7. The textile material of claim 1 wherein the bodily fluid has a volume, and wherein the first layer is configured to draw at least 90% of the volume of the bodily fluid through the first layer to the second layer within five seconds of the volume of the bodily fluid contacting the inner surface of the first layer.

8. The textile material of claim 1, further comprising a fourth layer opposite the third layer from the second layer, the fourth layer including an interior surface and an exterior surface opposite the interior surface, wherein the fourth layer includes a water-repellant finish on the interior surface configured to at least partially block the bodily fluid from flowing through the fourth layer.

9. A garment configured to be used in containing a liquid expelled from a body, the garment comprising:
a first portion positioned in the garment to receive the liquid, the first portion including:
a first layer configured to contact the body, the first layer including a first knitted pattern having a plurality of channels configured to allow the liquid to flow in a first plane towards a plurality of pores that allow the liquid to flow in a direction generally orthogonal to the first plane;
a second layer opposite the first layer from the body, the second layer including a matrix of hydrophilic fibers in a second knitted pattern to disperse the liquid in a second plane generally parallel with the first plane and at least one section generally corresponding to at least one pore of the plurality of pores, the at least one pore extending through the section of the second layer;
a third layer opposite the second layer from the first layer, the third layer including a hydrophilic material configured to absorb the liquid from the second layer and hold the liquid in the third layer; and
a fourth layer opposite the third layer from the second layer, the fourth layer including a moisture-resistant material configured to at least partially block the liquid from moving through the fourth layer; and
a second portion attached to the first portion.

10. The garment of claim 9 wherein the garment is a pair of underwear, and wherein the first portion includes at least a crotch portion of the underwear.

11. The garment of claim 9 wherein the garment is a bra and wherein the first portion includes at least one cup of the bra.

12. The garment of claim 9 wherein the garment is a pair of compression shorts, and wherein the first portion includes at least a crotch of the compression shorts.

13. A textile material for managing a bodily fluid comprising:
a first layer configured to disperse the bodily fluid arriving at an inner surface of the first layer, wherein the first layer includes
a first material having a knitted pattern having a plurality of generally horizontal hydrophobic channels and a plurality of generally vertical hydrophobic channels, wherein the generally horizontal channels are configured to disperse the bodily fluid towards the generally vertical channels, and wherein the plurality of vertical channels are configured to draw the bodily fluid vertically away from the inner surface;
a second material in contact with the first material opposite the inner surface, the second material having a knitted matrix of hydrophilic fibers configured to receive the bodily fluid from the generally vertical channels, disperse the bodily fluid in a horizontal plane, and draw the bodily fluid towards an outer surface of the first layer, wherein:
the knitted matrix of hydropilic fibers has a first thread count on an upper portion of the second material adjacent to the first material and a second thread count higher than the first thread count on a lower portion of the second material spaced apart from the first material, and
at least one of the vertical channels extends from the inner surface to the outer surface through the second material; and
a second layer in contact with the outer surface, the second layer comprising a hydrophilic material configured to receive the bodily fluid from the first layer and contain the bodily fluid in the second layer; and
a third layer opposite the second layer from the first layer, the third layer including a moisture-resistant material in contact with the second layer, wherein the moisture-resistant material is configured to block the bodily fluid from flowing through the third layer.

14. The textile material of claim 13 wherein the hydrophilic material in the second layer is a first hydrophilic material in a first sublayer, and wherein the second layer further comprises a second hydrophilic material in a second sublayer.

15. The textile material of claim 14 wherein the first hydrophilic layer has a first material density and the second hydrophilic material has a second material density higher than the first material density.

16. The textile material of claim 13 wherein the third layer is laminated directly onto the second layer.

17. The textile material of claim 13, further comprising a fourth layer opposite the third layer from the second layer, the fourth layer including an interior surface and an exterior surface opposite the interior surface, wherein the fourth layer includes a water repellant finish on the interior surface configured to at least partially block the bodily fluid from flowing through the fourth layer.

18. The garment of claim 9 wherein the first knitted pattern is different from the second knitted pattern.

* * * * *